(12) United States Patent
Thwaite

(10) Patent No.: US 8,827,555 B2
(45) Date of Patent: Sep. 9, 2014

(54) METHOD OF CALIBRATING A RADIOTHERAPY SYSTEM

(75) Inventor: Graham Thwaite, Crawley (GB)

(73) Assignee: Elekta AB (Publ), Stockholm (SE)

( * ) Notice: Subject to any disclaimer, the term of this patent is extended or adjusted under 35 U.S.C. 154(b) by 740 days.

(21) Appl. No.: 13/158,609

(22) Filed: Jun. 13, 2011

(65) Prior Publication Data

US 2012/0312974 A1   Dec. 13, 2012

(51) Int. Cl.
*A61B 6/00* (2006.01)
*A61N 5/10* (2006.01)

(52) U.S. Cl.
CPC .................................... *A61N 5/1075* (2013.01)
USPC ............................................ 378/207; 378/65

(58) Field of Classification Search
USPC .................................................... 378/65, 207
See application file for complete search history.

(56) References Cited

U.S. PATENT DOCUMENTS

| | | | |
|---|---|---|---|
| 6,125,335 A | 9/2000 | Simon et al. | 702/85 |
| 6,626,569 B2 | 9/2003 | Reinstein et al. | 378/206 |
| 7,729,472 B2 * | 6/2010 | Scherch et al. | 378/65 |
| 7,801,269 B2 | 9/2010 | Cravens et al. | 378/65 |
| 8,321,179 B2 * | 11/2012 | Simon et al. | 702/189 |

FOREIGN PATENT DOCUMENTS

WO    WO 2010/006630 A1    1/2010    ............... H05H 9/00

* cited by examiner

*Primary Examiner* — Hoon Song
(74) *Attorney, Agent, or Firm* — Sunstein Kann Murphy & Timbers LLP

(57) ABSTRACT

The present invention provides a method of calibrating a radiotherapy apparatus, in which a beam measurement device is accurately located with respect to the radiation beam center. The method comprises acquiring the center of the radiation beam at two angles of rotation, separated by 180°, and aligning a beam measurement device with the midpoint of the respective centers.

9 Claims, 4 Drawing Sheets

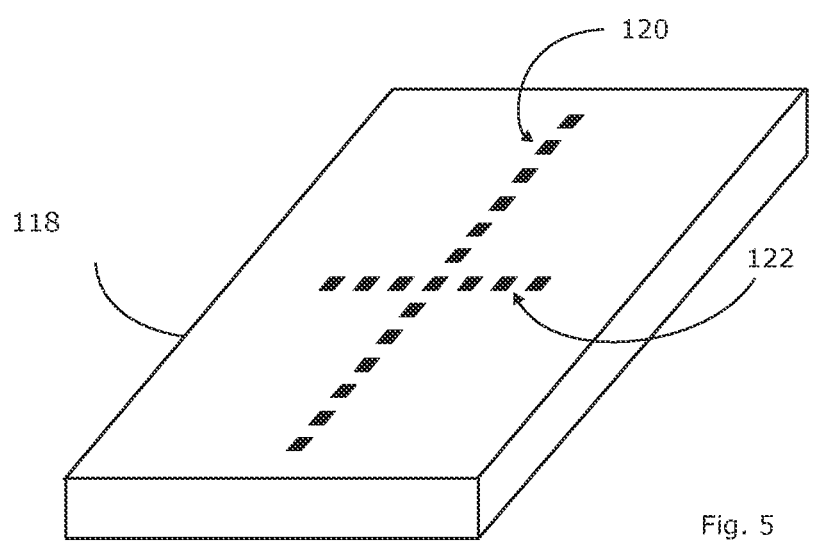

METHOD OF CALIBRATING A RADIOTHERAPY SYSTEM

FIELD OF THE INVENTION

The present invention relates to a method of calibrating a radiotherapy system.

BACKGROUND ART

Radiotherapy is the use of highly ionizing radiation to damage or kill diseased (e.g. cancerous) cells in a patient. In one form of radiotherapy, a linear accelerator is employed to accelerate charged particles either towards the patient (in which case the charged particles themselves act as the therapeutic radiation) or towards an x-ray target (in which case the x-rays so generated have the therapeutic effect). The radiation is highly damaging to all cells in its path (i.e. both healthy and unhealthy), so the shape and direction of the radiation must be carefully controlled to conform to precise standards.

As part of this process, the radiation is usually first collimated into a beam (cone- and fan-shaped beams are well known in the art, but other shapes are possible) by so-called "primary" collimators, and then further collimated to conform to the shape of a target region within the patient by one or more secondary collimators (e.g. multi-leaf collimators). Considerable research and effort is spent in ensuring the radiation is as closely focussed on the target region as possible, so that damage to the surrounding healthy tissue is minimized. For example, it is known to integrate imaging systems with radiotherapy to provide real-time feedback of the target position. However, the benefits of such systems are significantly reduced if the radiation beam itself is incorrectly calibrated from the start.

When a linear accelerator (linac) is set up, the beam position needs to be measured to prove that it meets the PTS (Production Test Schedule) specification. Conventionally, this is done using a single ion chamber that is scanned through the beam. The chamber is aligned by eye to the projection of a cross wire which had itself been aligned (by eye) to the centre of the beam. This method has an inherent build-up of tolerances of ~2 mm (for example in the backlash of the scanning movement, and in the alignment by eye).

It is an object of the present invention to provide a more accurate, repeatable method of calibrating the linear accelerator.

SUMMARY OF THE INVENTION

Modern beam measurement devices can provide a wider surface area, to the point where scanning of the device across the beam is no longer necessary; eliminating the errors associated with backlash. For example, an ion chamber array (such as that described by U.S. Pat. No. 6,125,335) can be used to provide a detecting device with a wide cross-sectional area. This is a flat bed of multiple ion chambers arranged along the major axes that would previously have been scanned. As the array has no moving parts there are no backlash issues as with the scanning ion chamber.

This does not provide a solution to the alignment of the beam measurement device with the radiation head, however. As we now have a repeatable method of measuring the beam without the mechanical variation of a scanning ion chamber being an issue, it would be better if the beam measurement device (i.e. the ion chamber array) could be located in the same position every time, relative to the head of the gantry (not relative to the beam—this is what we want to use to align the beam). This would give a better consistency of machine set up.

Methods were considered in which a so-called "flattened" radiation beam is used. However, a diaphragm edge is required to flatten the beam, and at such an early stage of calibration the diaphragm location may not be accurately known.

The present invention provides a method of calibrating a radiotherapy apparatus, in which a beam measurement device is accurately located to coincide with the centre of a desired beam axis. The centre of the radiation beam is determined, the radiation head (to which the beam measurement device is coupled) rotated by 180°, and the centre of the radiation beam determined again. The beam measurement device may then be repositioned so that it is aligned with the midpoint of the relative displacement of the two centres.

In one aspect, the present invention provides a method of calibrating a radiotherapy system, the radiotherapy system comprising a source of radiation producing a beam of radiation along a beam axis and a radiation head comprising a collimating apparatus for collimating the beam of radiation. The method comprises placing a beam measurement device in the path of the beam of radiation and coupling the beam measurement device to the radiation head such that rotation of the radiation head causes corresponding rotation of the beam measurement device; determining a first location of a centre of the beam of radiation in said beam measurement device; rotating the radiation head by 180° around an axis coincident with a desired beam axis; determining a second location of the centre of the beam of radiation in said beam measurement device; calculating a displacement of said second location from said first location; and adjusting the lateral displacement of the beam measurement device such that said beam measurement device is aligned with the midpoint of said displacement.

In an embodiment, the method further comprises adjusting the angle of the radiation beam such that a centre of the radiation beam coincides with said midpoint.

In an embodiment, the method further comprises prior to said calculating step, rotating the radiation head by 180° around said axis; determining a third location of the centre of the beam of radiation in said beam measurement device; determining the displacement of said third location from said first location; comparing the displacement to a threshold value; and, if said displacement exceeds said threshold value, aborting or restarting the method. In embodiments of the present invention, the threshold value is 0.3 mm, although any alternative appropriate value may be used in practice.

In embodiments of the present invention, the radiation beam has a uniform cross-section during calibration; that is to say, the multi-leaf collimator leaves and/or diaphragms, which are commonplace in radiotherapy to shape the radiation beam for therapy, are either withdrawn entirely from the radiation field or form a uniform square or circular window for radiation to pass through.

In an embodiment, the beam measurement device comprises an array of ion chambers. This may form an array of ion chambers formed in an M×N array (where M and N are positive integers), or in a single row of M ion chambers and a single column of N ion chambers, arranged orthogonally. A further example has several lines of M ion chambers sharing a common central chamber and aligned at 45 degree intervals to one another.

Various methods may be employed to determine the centre of the radiation beam. In one embodiment, the centre of the beam of radiation is determined by determining the gradient of the beam profile at a plurality of locations, and determining the point of intersection of said gradients. These points of intersection may be averaged to determine the centre. In still further embodiments, the centre of the beam of radiation is an average of the centre of the beam of radiation at a plurality of beam energies.

BRIEF DESCRIPTION OF THE DRAWINGS

An embodiment of the present invention will now be described by way of example, with reference to the accompanying figures in which;

FIG. 5 shows an example of a beam measurement device which may be used in methods according to embodiments of the present invention.

DETAILED DESCRIPTION OF THE EMBODIMENTS

Figure 1:
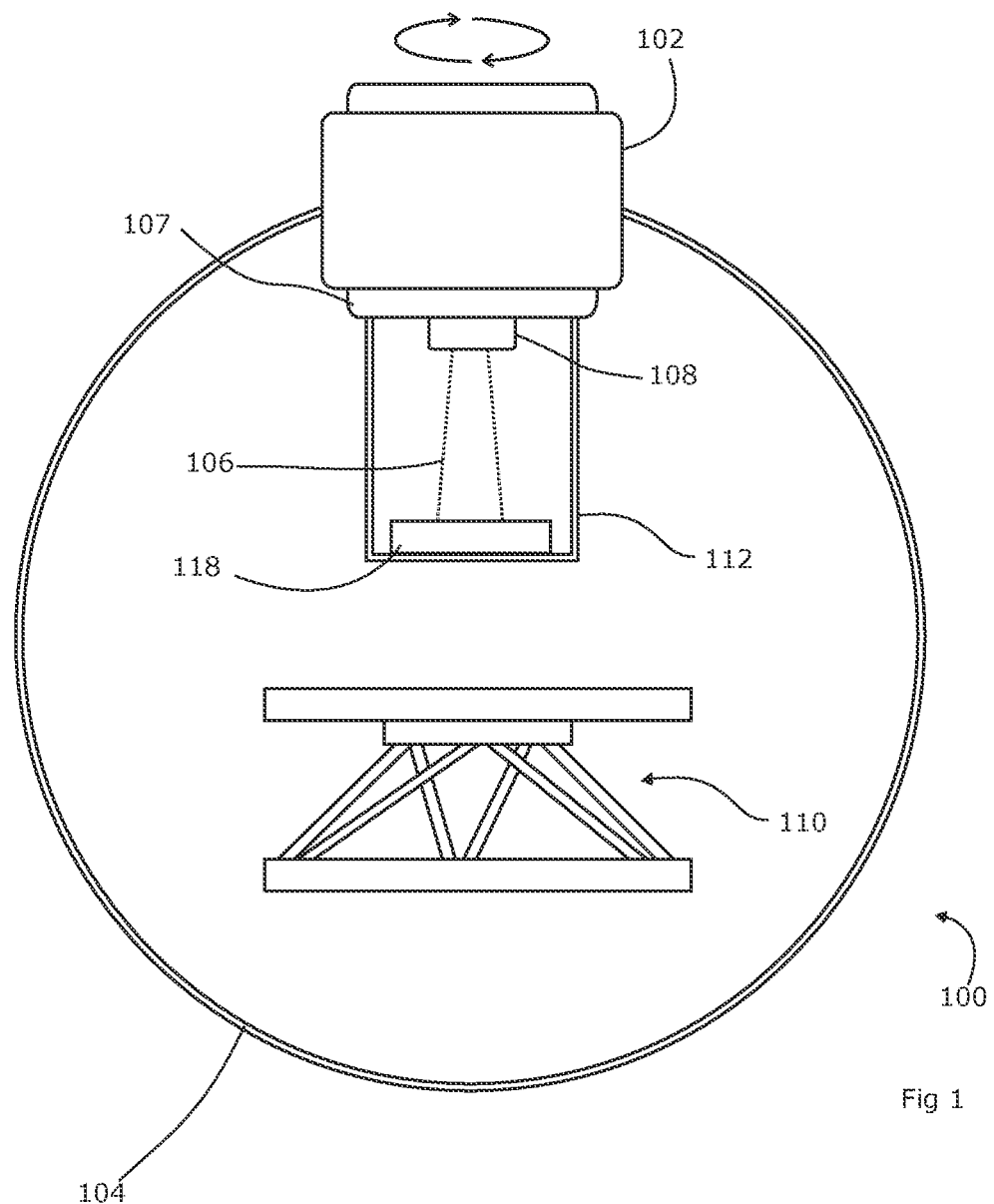
FIG. 1 shows a radiotherapy apparatus undergoing calibration.

FIG. 1 shows one example of a radiotherapy apparatus 100 such as may be calibrated by methods according to embodiments of the present invention.

The radiotherapy system comprises a source of ionizing radiation 102, mounted on a gantry 104 and arranged to produce a beam of radiation 106. A support apparatus 110 is provided to support a patient during treatment, and as such is positioned to intersect the radiation beam 106. Depending on the form of treatment provided, the gantry 104 may be able to rotate so as to direction radiation towards the target from multiple directions. However, the method according to embodiments of the present invention does not rely upon such rotation, and therefore the present invention is applicable to radiotherapy systems where the radiation head is in a fixed position relative to the patient. What is required is that the radiation head 102 is able to rotate about an axis which is approximately coincident with the axis of the radiation beam (see the arrows in FIG. 1). This rotation will be explained in greater detail below.

The source of ionizing radiation 102 (such as, for example, a linear accelerator with or without an x-ray target) comprises various "primary" collimating apparatus to focus that ionizing radiation into a beam of desired shape for treatment. It is known in the art to first collimate the radiation into a beam having a uniform shape; for example, both cone beams (in which the radiation diverges from the beam axis substantially equally in all directions) and fan beams (in which the radiation diverges from the beam axis to a greater extent in one direction than the other) are known. Subsequent to that "primary" collimation, secondary collimation is used during treatment to further shape the beam to conform to a shape desired for treatment. For example, the tissue selected for treatment in a patient will generally not have a cone (i.e. circular) or fan shape; radiative dose to the healthy tissue surrounding the target can therefore be reduced by shaping the beam appropriately.

For this purpose, a radiation head 107 is coupled to the source of radiation 102, providing a second collimating apparatus 108. Various means for secondary collimation exist in the art, but the most common is the multi-leaf collimator. This device consists of a housing having a window which defines the passage of the radiation beam, and one or more banks of thin, elongate leaves. The leaves are relatively thick in the direction of the radiation beam, however, and manufactured from a material of high atomic number such as tungsten. A common arrangement is to provide two banks of leaves on opposite sides of the window. Each leaf is individually controllable to take a position relative to the window: extending across the window (and therefore blocking the radiation beam), lying outside the window (and therefore providing no collimating effect) or somewhere in between. By controlling the leaves suitably, the shape of the radiation beam can be collimated to a desired shape. Dynamic control of the leaves during treatment allows the radiation beam to track motion of the target, owing to movement of the patient and/or the gantry 104.

As described earlier, radiotherapy works by directing high-energy ionizing radiation towards a target region in a patient. The radiation has a deleterious effect on all cells in its path (both healthy and unhealthy), and therefore the radiation beam should be directed as accurately as possible towards the unhealthy tissue. Various means exist for achieving this, for example by controlling the MLC leaf positions during treatment. However, such control is ineffective if one cannot predict the position and extent of the radiation beam without collimation by the MLC leaves. Therefore, prior to treatment, some calibration of the radiotherapy system is required.

It will be seen from FIG. 1, therefore, that a frame 112 has been connected to the radiation head 107, and a beam measurement device 118 placed on the frame 112 as part of the calibration process.

Figure 2:
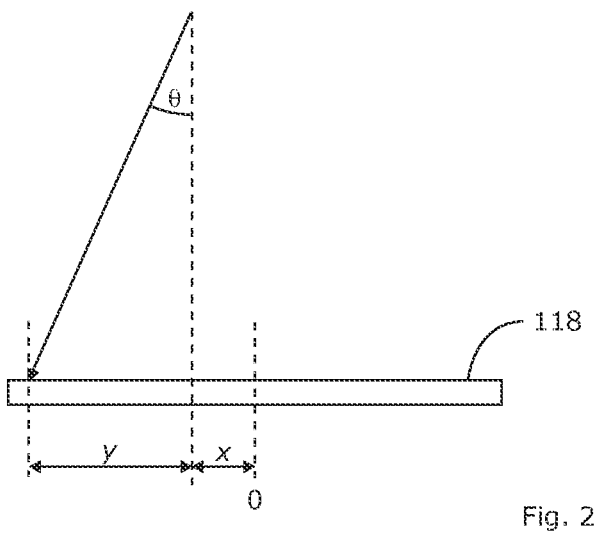
FIG. 2 is a schematic diagram showing calibration according to embodiments of the present invention in one dimension.

FIG. 2 shows the extent of the problem in one dimension (i.e. a side-on view). The axis of the radiation beam is illustrated by a solid arrow. Ideally, the radiation beam should be aligned perpendicularly to and through the centre of the beam measurement device 118 (and therefore, during treatment, the patient). At the point of setup, however, neither of those things will be true in general. As can be seen from FIG. 2, the radiation beam may be arranged at a slight angle θ to the perpendicular, resulting in an offset at the beam measurement device 118 due to angular misalignment of Y (the effect is greatly exaggerated in FIG. 2 for purposes of clarity). In addition to that offset, the radiation beam may have a mechanical misalignment of X from the centre of the beam measurement device, labelled "0".

Figure 3:
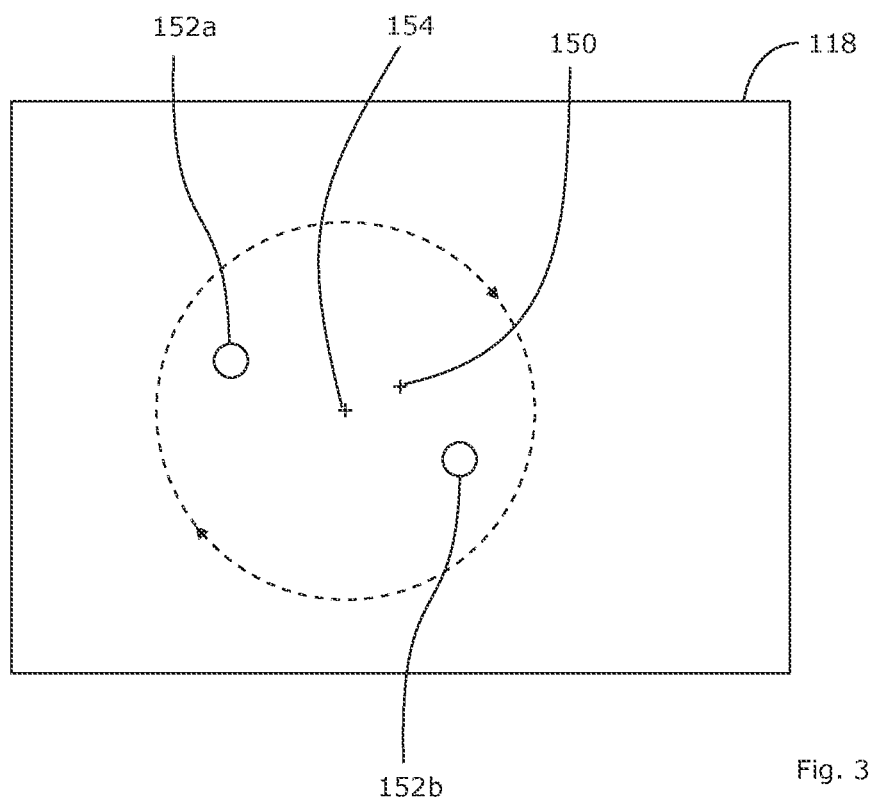
FIG. 3 is a schematic diagram showing calibration according to embodiments of the present invention in two dimensions.
Figure 4:
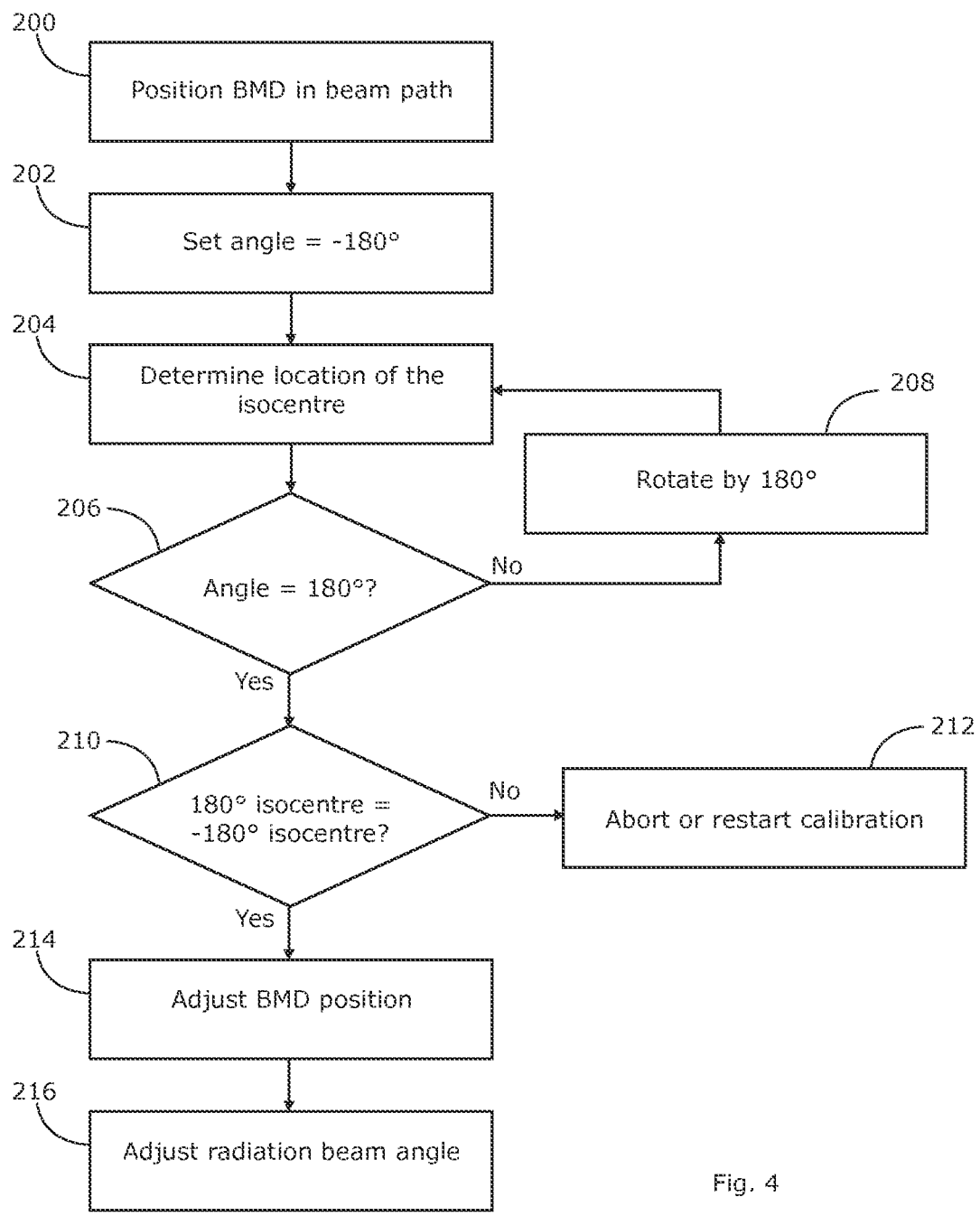
FIG. 4 is a flow chart of a method according to embodiments of the present invention.

FIG. 3 shows the same principle in two dimensions, where the view is approximately along the beam axis. FIG. 3 also shows some of the principles of the present invention, and thus will be described in greater detail with respect to FIG. 4, a flowchart of a method according to embodiments of the present invention.

The method begins in step 200, where a beam measurement device 118 is placed in the path of the radiation beam (or the expected path of the radiation beam), in a frame 112 attached to the radiation head 107. Precise alignment is not required at this stage, so it is a straightforward task to place the device approximately in line with the radiation beam by eye. The centre of the beam measurement device 118 is indicated by the label 150.

In the next step 202, the angle of the radiation head 107 (and thus also the collimator 108, the frame 112 and the beam measurement device 118) is set to −180°. Note that this angle is a nominal angle without significance at this stage of the method. Thus in practice any angle can be selected in step 202. In step 204, the radiation source 102 is activated and a radiation beam generated which falls on the beam measurement device 118. The radiation beam used in this step is collimated only to the extent required in order to form the general beam shape (i.e. primary collimation discussed above, to generate a fan or cone beam for example). No secondary collimation takes place using the multi-leaf collimator 108, so the beam takes what is known as a "raw" beam profile. Alternatively, a small amount of secondary collimation may take place to uniformly reduce the extent of the beam width; for example, the secondary collimator 108 may allow a square- or circular-shaped radiation beam to pass through to the beam measurement device 118. The beam measurement device detects the radiation, and the centre 152a of the beam can be calculated from the detected data (i.e. where the radiation intensity is greatest). Methods for determining the centre will be described in greater detail below.

In step 206, it is determined whether the angle of the radiation head is equal to +180°. Of course, in the first instance that will not be the case; the angle was set to −180° in step 202. The method therefore proceeds to step 208, where the radiation head 107 is rotated by 180° about an axis 154. Note that the radiation head 107 is rotated, not the source of radiation 102. Thus the radiation should remain in a fixed location. It can be seen from FIG. 3 that the axis is approximately coincident with the centre of the radiation beam; ultimately the radiation beam should be accurately centred on the rotation axis 154 and therefore perpendicular to the radiation head 107.

Once rotated, the location of the centre of the radiation beam is determined again in step 204. It can be seen in FIG. 3 that the centre has moved to a new position 152b which is diametrically opposite the original location relative to the axis of rotation 154.

Again, however, the angle is not equal to +180° so the radiation head is rotated by 180° for a second time in step 208. The isocentre is acquired again in step 204 and this time the decision step 206 can be answered positively; the angle of the radiation head 107 is equal to +180°. The process has thus far acquired the isocentre of the radiation beam at three angles: −180°, 0° and +180°. Those skilled in the art will appreciate the method does not preclude the acquisition of the isocentre at further angles of rotation (e.g. at intervals of) 90°, but does not require it.

The isocentres at angles −180° and +180° are compared in step 210. As the two angles are essentially the same, the isocentre location in each case should be identical (to within a threshold amount, say 0.3 mm). If the isocentre has moved by more than the threshold amount, the calibration will be invalid and the process is aborted or restarted in step 212. If the centres are in the same location, the beam can be assumed to have stayed stationary throughout the rotation of the radiation head, and the process moves to step 214. In this step, by analysing the displacements of the radiation centres at angles of −180° and 0°, it is possible to distinguish the contributions of its two components: the angle of the radiation beam, and the displacement of the beam measurement device 118 from the rotation axis of the head. The rotation axis of the radiation head is equal to the midpoint of the displacement of the centres at these two angles. The beam measurement device 118 may then be repositioned so that its centre coincides with the calculated rotation axis.

Once the beam measurement device 118 is correctly aligned with the radiation head 107, further calibration can take place to adjust the angle of the radiation beam (step 216), the positions of the collimator 108, etc. Such further steps will be apparent to the skilled reader.

One suitable beam measurement device 118 for use in the methods described above is shown in FIG. 5. Although beam measurement devices in general may comprise an M×N array of sensor elements (such as ion chambers), where M and N are positive integers, in practice it is unnecessary to provide such a large number of elements. Costs and complexity can be reduced by providing a single column of sensor elements and a single row of sensor elements in mutually orthogonal directions. In the illustrated embodiment, the beam measurement device 118 comprises a single column of ion chambers 120 and a single row of ion chambers 122 arranged in a cross. The centre of the beam can be calculated by determining the centre of the beam in each orthogonal direction, and taking those values as the (x, y) coordinates of the radiation beam centre.

In general, locations nearer the centre of the radiation beam will receive a greater radiation dose than locations further from the centre. This gives rise to a beam profile, in which locations near the centre receive a dose which is a higher percentage of the maximum dose and locations further from the centre receive a dose which is a lower percentage of the maximum dose.

In an embodiment, the centre of the radiation beam may be determined as follows. For each row of sensor elements 120, 122, the gradient of the beam profile is measured at two locations on opposite sides of the centre corresponding to a particular dose percentage point. The intersection of those gradients (assuming a constant gradient) can then be taken as one indication of the centre location. However, the gradient may not be constant, so the process is repeated for one or more different percentage points, corresponding to different pairs of locations in the rows of sensors. For each pair, the gradient is measured and the intersection calculated. The centre of the radiation beam in each direction may then be determined by calculating the mean average of each intersection.

Still further variation of the centre may occur by varying the energy of the radiation beam. The beam profile will not generally stay constant for different energies, and therefore the process described above may be repeated for multiple energies, with the centre of the radiation beam determined as the average of the centre at each energy.

The present invention therefore provides a method of calibrating a radiotherapy apparatus, in which a beam measurement device is accurately located with respect to the radiation beam centre. Further calibration of the radiotherapy apparatus can then proceed on a more accurate footing.

It will of course be understood that many variations may be made to the above-described embodiment without departing from the scope of the present invention.

The invention claimed is:

1. A method of calibrating a radiotherapy system, the radiotherapy system comprising a source of radiation producing a beam of radiation along a beam axis, and a radiation head comprising a collimating apparatus for collimating the beam of radiation, the method comprising:

placing a beam measurement device in the path of the beam of radiation, and coupling the beam measurement device to the radiation head such that rotation of the radiation head causes corresponding rotation of the beam measurement device;

determining a first location of a centre of the beam of radiation in said beam measurement device;

rotating the radiation head by 180° around an axis coincident with a desired beam axis;

determining a second location of the centre of the beam of radiation in said beam measurement device;

calculating a displacement of said second location from said first location; and adjusting the lateral displacement of the beam measurement device such that said beam measurement device is aligned with the midpoint of said displacement.

2. The method according to claim 1, further comprising:

adjusting the angle of the radiation beam such that a centre of the radiation beam coincides with said midpoint.

3. The method according to claim 1, further comprising:

determining whether said radiation beam complies with a required specification.

4. The method according to 1, further comprising:

prior to said calculating step, rotating the radiation head by 180° around said axis;

determining a third location of the centre of the beam of radiation in said beam measurement device;

determining the displacement of said third location from said first location;

comparing the displacement to a threshold value; and if said displacement exceeds said threshold value, aborting or restarting the method.

5. The method according to claim 4, wherein the threshold value is 0.3 mm.

6. The method according to claim 1, wherein said radiation beam has a uniform cross-section.

7. The method according to claim 1, wherein the beam measurement device comprises an array of ion chambers.

8. The method according to claim 1, wherein the centre of the beam of radiation is determined by determining the gradient of the beam profile at a plurality of locations, and determining the point of intersection of said gradients.

9. The method according to claim 1, wherein the centre of the beam of radiation is an average of the centre of the beam of radiation at a plurality of beam energies.

* * * * *